United States Patent [19]

Monticello et al.

[11] Patent Number: 5,529,930

[45] Date of Patent: Jun. 25, 1996

[54] BIOCATALYTIC PROCESS FOR REDUCTION OF PETROLEUM VISCOSITY

[75] Inventors: Daniel J. Monticello, The Woodlands, Tex.; William M. Haney, III, Boston, Mass.

[73] Assignee: Energy BioSystems Corporation, The Woodlands, Tex.

[21] Appl. No.: 69,295

[22] Filed: May 28, 1993

Related U.S. Application Data

[63] Continuation-in-part of Ser. No. 631,642, Dec. 21, 1990, abandoned.

[51] Int. Cl.$^6$ .................. C10G 32/00; C10G 29/20; C02F 3/00; C02F 3/02
[52] U.S. Cl. .................. 435/281; 435/262; 435/252.1; 208/44; 208/237; 210/601; 210/611
[58] Field of Search .................. 435/262, 281, 435/282, 252.1; 208/237, 44; 210/601, 611

[56] References Cited

U.S. PATENT DOCUMENTS

| | | | |
|---|---|---|---|
| 2,975,103 | 3/1961 | Kirshenbaum | 195/3 |
| 3,069,325 | 12/1962 | Hitzman | 195/3 |
| 4,498,906 | 2/1985 | Scheffee | 44/51 |
| 4,562,156 | 12/1985 | Isbister et al. | 435/253 |
| 4,615,791 | 10/1986 | Choi et al. | 208/107 |
| 4,618,348 | 10/1986 | Hayes et al. | 44/51 |
| 4,632,906 | 12/1986 | Kopacz | 435/282 |
| 4,659,670 | 4/1987 | Stevens, Jr. et al. | 435/262 |
| 5,002,888 | 3/1991 | Kilbane | 435/252.31 |
| 5,104,801 | 4/1992 | Kilbane | 435/282 |
| 5,132,219 | 7/1992 | Kilbane | 435/195 |
| 5,198,341 | 3/1993 | Kilbane | 435/42 |
| 5,232,854 | 8/1993 | Monticello | 435/282 |
| 5,356,801 | 10/1994 | Ramboseh et al. | 435/195 |
| 5,356,813 | 10/1994 | Monticello | 435/282 |
| 5,358,870 | 10/1994 | Monticello et al. | 435/282 |
| 5,387,523 | 2/1995 | Monticello | 435/282 |

FOREIGN PATENT DOCUMENTS

| | | | |
|---|---|---|---|
| 9209706 | 6/1992 | WIPO | C12S 1/00 |

OTHER PUBLICATIONS

Omoni et al. "Desulfurization of Dibenzothiophene by Corynebacterium sp strain Sy1." Applied and Environmental Microbiology Mar., 1992. pp. 911–915.

Haksuron Nonmunjys (12) pp. 73–75 1973 Abstract.

Cheng et al. "Biotechnological Methods of upgrading bitumen" Chemical Abstracts 112:121829. 1989.

Bertrand, et al., "Microbial Degradation of Crude Oil in Sea Water in Continuous Culture", *bioTechnology Letters*, 5(8):567–572 (1983).

J. H. Gary and G. E. Handwerk, "Petroleum Refining: Technology and Economics", Marcel Dekker, Inc., New York, Chapter 8, pp. 114–119 (1975).

D. J. Monticello and W. R. Finnerty, "Microbial Desulfurization of Fossil Fuels", *Ann. Rev. Microbiol.*, 39:371–389 (1985).

Kilbane, "Sulfur–Specific Microbial Metabolism of Organic Compounds", presented at the *Bioprocessing of Coals Workshop*, (1988).

Kilbane, "Biodesulfurization of Coal", presented at the *Institute of Gas Technology Symposium on Gas, Oil and Coal Biotechnology*, (1988).

Kilbane, "Sulfur–Specific Microbial Metabolism of Organic Compounds", *Resources, Conservation and Recycling*, 3:69–79 (1990).

Monticello et al., "Practical Considerations in Biodesulfurization of Petroleum", presented at the *Institute of Gas Technology's Third International Symposium on Gas, Oil, Coal and Environmental Biotechnology*, (1990).

Lee et al., "Sulfur Removal from Coal Through Multiphase Media Containing Biocatalysts", *J. Chem. Tech. Biotechnol.*, 48:71–79 (1990).

Kilbane, "Desulfurization of Coal: The Microbial Solution", *Trends in Biotechnology*, 7(4):97–101 (1989).

Kargi et al., "Microbial Oxidation of Dibenzothiophene by the Thermophilic Organism *Sulfolobus acidocaldarius*", *Biotechnology and Bioengineering*, 26:687–690 (1984).

Isbister et al., "Microbial Desulfurization of Coal", *The First International Conference on Processing and Utilization of High Sulfur Coals*, (1985).

Kilbane, "Biodesulfurization: Future Prospects in Coal Cleaning", presented at the *Pittsburgh Coal Conference*, 1990.

*Primary Examiner*—Donald E. Czaja
*Assistant Examiner*—T. J. Reardon
*Attorney, Agent, or Firm*—Hamilton, Brook, Smith & Reynolds

[57] ABSTRACT

A method for reducing the viscosity of viscous petroleum liquids, such as heavy crude oil and bitumen, is disclosed. The method is appropriate for use with viscous petroleum liquids that contain sulfur-bearing heterocycles, the physicochemical properties of the heterocycles contributing significantly to the viscosity of the liquid. The method comprises contacting the viscous petroleum liquid with a biocatalyst that converts sulfur-bearing heterocycles into molecules that lack physicochemical properties condusive to viscosity. The biocatalyst works in a sulfur-specific manner, such that the sulfur-bearing heterocycle is altered at the sulfur heteroatom thereof. Through biocatalysis, carbon-sulfur bonds are cleaved and/or polar substituents such as hydroxyl groups are joined to the sulfur heteroatom, the hydrocarbon framework of the sulfur-bearing heterocycle, or both. Preferred biocatalysts for viscosity reduction include preparations of *Rhodococcus rhodochrous* ATCC No. 53968 microorganisms and enzymes obtained therefrom.

17 Claims, 1 Drawing Sheet

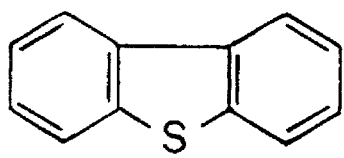
FIG. IA
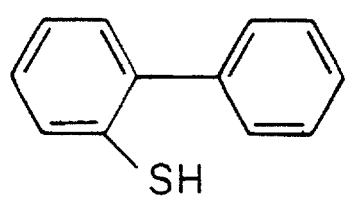
FIG. IB
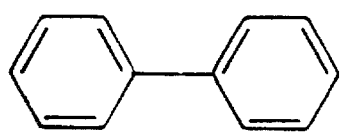
FIG. IC
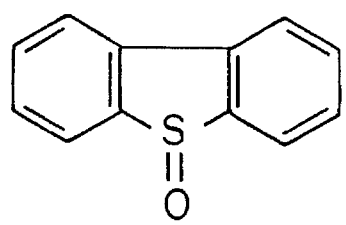
FIG. ID
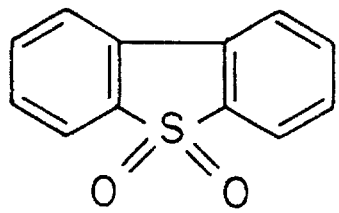
FIG. IE
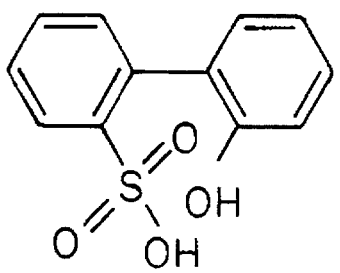
FIG. IF
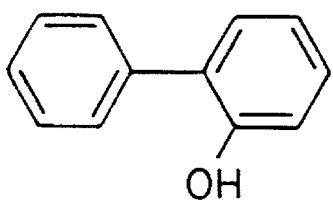
FIG. IG
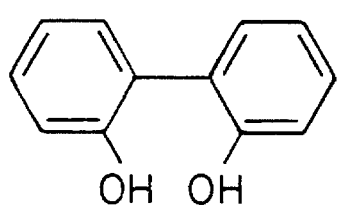
FIG. IH

BIOCATALYTIC PROCESS FOR REDUCTION OF PETROLEUM VISCOSITY

RELATED APPLICATIONS

This is a continuation-in-part of U.S. application Ser. No. 07/631,642, filed Dec. 21, 1990, now abandoned the teachings of which are incorporated by reference herein.

BACKGROUND

The high viscosity of many petroleum liquids is a factor contributing significantly to the underutilization of these valuable natural resources. Viscosity greatly complicates, and may even defeat, the extraction of many types of petroleum from the Earth. Viscosity remains a concern following extraction, as high viscosity significantly hampers the pumping, transportation, refining and handling of petroleum. Examples of viscous petroleum that can only be extracted and/or refined with great difficulty include Cerro Negro heavy crude oil, Orinoco heavy crude oil, and bitumens such as Athabascan tar. Because of this, the petroleum industry has long recognized the need for a safe, economical and effective method for reducing the viscosity of valuable fossil fuel resources.

Under certain circumstances, standard refining processes such as hydrotreating or hydrodesulfurization (HDS) can favorably affect the viscosity of petroleum liquids during refining. Hydrotreatment involves the exposure of petroleum to hydrogen gas in the presence of a metal catalyst, under conditions of elevated temperature and pressure. Reduced viscosity, when observed, is largely the result of the increased temperature to which the petroleum refining fraction is exposed. Some reduction in viscosity is also achieved through the breakdown of complex hydrocarbons (e.g., aromatic hydrocarbons), into simpler hydrocarbons of low molecular weight. Hydrotreating is not a refining process that was developed for the reduction of petroleum viscosity, however, and viscosity reduction is only an incidental side benefit that is occasionally observed and is poorly controllable or reproducible. Furthermore, hydrotreating is useful only at a limited number of steps in the refining of petroleum, due to the extreme conditions involved and the specialized containment and safety equiptment required.

A more generally accepted and controllable method of modulating petroleum viscosity during refining involves diluting viscous petroleum liquids with low viscosity petroleum refining fractions, usually light-end distillates. Light-end distillates that are used as viscosity lowering diluents are referred to as cutter fractions. Thus, the viscosity of heavy crude oil or bitumen is lowered by "cutting" it with such a light-end distillate. This technique is useful at some stages of the petroleum refining process, but is not economical for large-scale use, or to assist with the extraction of viscous petroleum liquids from the earth.

Other techniques which have been developed for the control of high viscosity in petroleum liquids center on the use of chemical additives such as the tensioactive compounds (surfactants) described by R. S. Scheffee in U.S. Pat. No. 4,498,906. Scheffee discloses a combustible formulation in which surfactants of biological origin are added at the close of the refining process. The use of such chemical additives at earlier stages of the extraction and refining of petroleum is prohibited by expense and by the need to remove surfactants in order to subject the petroleum to certain standard refining procedures. Surfactant recovery greatly complicates the refining process.

Various investigators, e.g., Bertrand et al. (1983), 5 BIOTECH. LETT. (No. 8) 567–572, have described the production of biosurfactants in situ by microbial organisms grown in the presence of crude oil. These biosurfactants assist in the dispersal of crude oil in seawater, thus facilitating the bioremediation of oil spills and chronic petroleum pollution. Microorganisms used for bioremediation purposes, however, are not generally compatible with petroleum extraction and refining processes, because they also attack and catabolize (destroy) combustible hydrocarbons.

Other types of microorganisms have been used for the relatively controlled destruction of certain compounds in petroleum, with the result that viscosity of the treated product is stabilized. For example, D. O. Hitzmann in U.S. Pat. No. 3,069,325 describes a method for stabilizing the viscosity of jet fuels when stored, as in military installations, over seawater. The viscosity of untreated jet fuels increases upon exposure to such storage conditions, due to the accumulation of a sludge composed of natural bacteria present in the seawater that attack the stored fuel as a source of nutrients such as carbon, nitrogen, and sulfur. This sludge becomes dispersed within the fuel upon physical agitation, increasing its viscosity and therefore the risk of clogging jet engines. Hitzmann prevents the accumulation of this sludge by pretreatment of jet fuel with strains of bacteria adapted to the consumption of nitrogen- or sulfur-containing hydrocarbon fuel molecules as nutrient sources. When the nutrient-depleted fuel is thereafter stored over seawater, naturally occurring bacteria are unable to attack it as a metabolic substrate. Viscosity remains stable upon storage, but this result is achieved through the loss of combustible sulfur- and nitrogen-containing hydrocarbons. The Hitzmann method is thus unsuitable for use prior to or during the refining process, as it destroys a portion of the caloric value of the treated fuel.

Still other types of microorganisms have been described as usful in other aspects of petroleum refining, e.g., desulfurization. Virtually all of these function as in the Hitzmann process, by the controlled demolition of certain types of troublesome compounds found in petroleum. Microorganisms such as *Thiobacillus ferrooxidans* have been harnessed to the removal of pyritic sulfur, while others such as *Pseudomonas putida* have been investigated for the removal of organic sulfur from petroleum. Microbial desulfurization technology is reviewed in Monticello and Finnerty (1985), 39 ANN. REV. MICROBIOL. 371–389, and Bhadra et al. (1987), 5 BIOTECH. ADV. 1–27. Kilbane (1989), 7 TRENDS BIOTECHNOL. (No. 4) 97–101 provides commentary on recent developments in the field. Such desulfurizing microorganisms are not thought of by those involved in petroleum extraction and refining as effective in altering the physical properties, e.g., viscosity, of petroleum. Indeed, the ineffectiveness of such microorganisms for the control of viscosity is illustrated by E. P. Kopacz in U.S. Pat. No. 4,632,906: attempts to desulfurize a vacuum residual oil using *Bacillus sulfasportare* ATCC No. 39909 were ineffective or poorly effective, until the viscous petroleum liquid was cut with a light petroleum oil cutter fraction (column 4, lines 23–25). Moreover, desulfurizing microorganisms are used for the treatment of many types of fossil fuels for which viscosity is irrelevant (e.g., solids such as coal), arises from complex and diverse phenomena, or is already sufficiently low to prevent no obstacle to refining procedures (e.g., middle distillates such as FCC light cycle oil or No. 1 diesel fuel).

A need remains for a viscosity reducing treatment that can be used to facilitate the handling of viscous petroleum liquids at any desired stage of the extraction and/or refining processes. A suitable viscosity reducing treatment would not require specialized equipment or safety procedures, and would not degrade the caloric (fuel) value of the treated petroleum.

SUMMARY OF THE INVENTION

The invention described herein relates to a method for reducing the viscosity of a viscous petroleum liquid which contains sulfur-bearing heterocycles, wherein the physicochemical properties of said heterocycles contribute significantly to the viscosity of the petroleum liquid. The present method comprises combining the petroleum liquid with a biocatalyst that converts sulfur-bearing heterocycles into molecules having physicochemical properties that do not significantly contribute to the residual viscosity of the treated petroleum liquid. Thus, the invention reduces viscosity by acting directly upon a significant source of viscosity at the molecular level. There is no need for expensive chemical additives which must thereafter be removed. The treated petroleum liquid produced following treatment according to the present invention has a lowered (residual) viscosity that does not present a substantial obstacle to subsequent refining procedures.

The present biocatalyst acts upon sulfur-bearing heterocycles in a sulfur-specific manner. That is, the structure of the sulfur-bearing heterocycle is altered by the biocatalyst at the sulfur heteroatom thereof, and/or at one or more of the carbon-sulfur bonds by which said sulfur heteroatom is covalently linked to the surrounding hydrocarbon framework. In one embodiment, the biocatalyst is one which oxidizes the sulfur heteroatom(s) of said heterocycles to produce organic sulfoxides and/or organic sulfones. In a preferred emodiment, the biocatalyst is one which oxidatively cleaves at least one of the carbon-sulfur bonds adjacent to the sulfur heteroatom(s), thereby breaking open heterocyclic rings and producing organic sulfonates and/or oxygenated hydrocarbon molecules. Each of the above-mentioned molecular products of biocatalytic action differs from the originally-present sulfur-bearing heterocycles in that the physicochemical properties of said molecules do not contribute significantly to the residual viscosity of the treated petroleum liquid. Hence, the residual viscosity of the treated petroleum is significantly lower than the viscosity of a corresponding sample of the same petroleum liquid that has not been subjected to biocatalytic viscosity-lowering treatment.

The present invention is particularly well-suited to the reduction in viscosity of viscous petroleum, including heavy crude oil and bitumen. For the present method to operate beneficially to reduce viscosity, the viscosity of the heavy crude oil or bitumen to be treated must arise in significant part from the presence therein of sulfur-bearing heterocycles. Examples of viscous petroleum that can be beneficially treated by the present invention include Cerro Negro and Orinoco heavy crude oils and Athabascan tar.

The biocatalyst relied upon in the present invention can be a preparation of one or more microbial organisms expressing one or more enzymes that selectively cleave at least one carbon-sulfur bond in sulfur-bearing heterocycles, thereby breaking open heterocyclic rings and producing sites of free rotation in the molecules formed from sulfur-bearing heterocycles by biocatalytic action. Alternatively, the present biocatalyst can be a preparation of one or more enzymes obtained from such microbial organisms, or a preparation that is a mixture of such microbial organisms and enzymes. Preferably, the microbial organisms express one or more enzymes that selectively oxidize the sulfur heteroatoms of sulfur-bearing heterocycles, and/or selectively oxidatively cleave at least one of the carbon-sulfur bonds adjacent to said sulfur heteroatoms. One example of such a microbial organism, which is employed as the biocatalyst or the biocatalyst source in several preferred embodiments, is the bacterium *Rhodococcus rhodochrous* ATCC No. 53968 described in U.S. Pat. Nos. 5,104,801 and 5,132,219, the teachings of each of which are incorporated herein by reference. Other examples of suitable microorganisms include mutational and genetically engineered derivatives of *Rhodococcus rhodochrous* ATCC No. 53968. Any microorganism which functions in a similar manner to *Rhodococcus rhodochrous* ATCC No. 53968 can be used satisfactorily as the biocatalyst or biocatalyst source herein.

In the embodiments relying on the use of an oxidative biocatalyst, the oxygen tension of the viscous petroleum or of the mixture of viscous petroleum and biocatalyst can be supplemented by an external oxygen source if desired. Supplemental oxygen may be desirable to accelerate the rate of viscosity reduction, or to ensure that substantially all of the sulfur-bearing heterocycles in the viscous petroleum liquid in need of treatment are converted into molecules lacking physicochemical properties condusive to viscosity. Exogenous oxygen may not be needed if a reductive biocatalyst is employed, if the oxygen tension of the viscous petroleum is already sufficiently high to produce the desired result with an oxidative biocatalyst, or if the biocatalytic conversion of sulfur-bearing heterocycles need not be driven to completion before reaching an acceptably low residual viscosity.

The present invention has many desirable features and advantages, some of which have been mentioned previously. For example, the present viscosity reducing treatment can be used to aid or facilitate the extraction from the earth of viscous petroleum liquids that otherwise could not be extracted, or could be extracted only with difficulty. Thus, it expands the range of petroleum resources that are available for commercial exploitation. The invention can be used at many stages of petroleum extraction and/or refining. The viscosity reducing biocatalyst relied upon in the present method can be used at well heads or other extraction sites, pumped into well shafts or admixed with extracted viscous petroleum prior to, upon or following transit to a refining site. It can also be used to lower the viscosity of many viscous petroleum refining fractions and byproducts, allowing the production of commercially valuable fuels from sources that would otherwise be viewed as waste or as low-value products.

Most advantageously, biocatalytic treatment according to the present invention does not significantly degrade the fuel value of treated petroleum liquids. In this, the present biocatalyst is unlike many other microbial organism and enzyme preparations that have been developed for use in petroleum refining. Furthermore, harsh physical conditions such as elevated temperature and/or pressure are not needed for viscosity treatment according to the present invention. Mild physical conditions, e.g., ambient temperature and pressure, are sufficient for biocatalysis to occur. The invention will be more fully understood and appreciated with respect to the following Drawing and Detailed Description.

BRIEF DESCRIPTION OF THE DRAWING

FIGS. 1A–1H depict the chemical structures of compounds a–h, respectively. FIG. 1A depicts a representative sulfur-bearing heterocycle, dibenzothiophene (DBT, compound a), along with the chemical structures of molecules produced from DBT upon viscosity-reducing treatment according to the present invention. Reductive viscosity-reducing biocatalysts convert DBT into DBT sulfide (compound b) or biphenyl (compound c) or a mixture thereof under anaerobic conditions. Oxidative viscosity-reducing biocatalysts convert DBT into any one or a mixture of one or more of the following: DBT sulfoxide (compound d), DBT sulfone (compound e), DBT sulfonate (compound f), hydroxybiphenyl (compound g) or dihydroxybiphenyl (compound h).

DETAILED DESCRIPTION OF THE PREFERRED EMBODIMENTS

In the petroleum extraction and refining arts, the term "organic sulfur" is generally understood as referring to organic molecules having a hydrocarbon framework which includes one or more sulfur atoms (called heteroatoms). These sulfur atoms can be joined directly to the hydrocarbon framework, e.g., by one or more carbon-sulfur bonds, or can be present in a substituent joined to the hydrocarbon framework of the molecule, e.g., a sulfonyl group (which contains a carbon-oxygen-sulfur covalent linkage). The general class of organic molecules having one or more sulfur heteroatoms are sometimes referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked to adjacent carbon atoms in the hydrocarbon framework by aromatic carbon-sulfur bonds are referred to as "sulfur-bearing heterocycles". The sulfur that is present in many types of sulfur-bearing heterocycles is referred to as "thiophenic sulfur" in view of the five-membered aromatic ring in which the sulfur heteroatom is present. The simplest such sulfur-bearing heterocycle is thiophene, which has the composition $C_4H_4S$.

Dibenzothiophene (DBT, $C_{12}H_8S$) is a sulfur-bearing heterocycle that has a condensed, multiple aromatic ring structure in which a five-membered thiophenic ring is flanked by two six-membered benzylic rings, as shown in FIG. 1 (compound a). DBT is accepted in the relevant arts as a model compound illustrative of the behavior of the class of sulfur-bearing heterocycles encompassing DBT and alkyl- and/or aryl-decorated derivatives thereof in reactions involving thiophenic sulfur. Monticello and Finnerty (1985), Microbial desulfurization of fossil fuels, 39 ANNUAL REVIEWS IN MICROBIOLOGY 371–389, at 372–373. In the alkyl- and/or aryl-decorated derivatives of DBT, one or more alkyl or aryl radicals are attached to one or more of the carbon atoms present in one or both flanking benzylic rings. DBT is particularly relevant as a model compound for the forms of thiophenic sulfur found in petroleum, such as crude oils, coals or bitumen of particular geographic origin, and various refining intermediates and fuel products obtained therefrom. Id.

The viscous petroleum liquids for which biocatalytic viscosity reducing treatment according to the present invention is suitable contain sulfur-bearing heterocycles, and the physicochemical properties of these organosulfur compounds contribute significantly to the observed viscous behavior of the liquid. Sulfur-bearing heterocycles such as DBT exist as rigid, planar condensed ring structures, which tend to form stable, highly organized intermolecular interactions (hydrophobic or van der Waals interactions) in liquids. As a result, such liquids do not flow readily when subjected to physical forces such as pressure or vacuum. Petroleum liquids that contain sufficiently high concentrations of sulfur-bearing heterocycles acquire semi-solid characteristics and are referred to as tars. Viscous petroleum liquids in which viscosity arises in significant part from the presence therein of sulfur-bearing heterocycles (predominantly DBT and alkyl/aryl decorated derivatives thereof) include Cerro Negro and Orinoco heavy crude oils and Athabascan tar. Viscous refining intermediates of these and other types of petroleum liquids also acquire their viscous behavior from the presence of sulfur-bearing heterocycles; examples of these intermediates include atmospheric and vacuum distillate residua and asphaltenes.

In each of the above petroleum liquids, the presence of sulfur-bearing heterocycles is a significant contributing cause of observed viscosity, although many other secondary contributing factors may also be present. Thus, biocatalytic conversion of sulfur-bearing heterocycles present in these liquids into molecules having physicochemical properties that do not produce viscosity is sufficient for the manufacture of a treated petroleum liquid having a residual viscosity that is significantly lower than that of the corresponding untreated petroleum liquid.

The biocatalyst employed in the present invention acts in a sulfur-specific manner. In other words, the present biocatalyst chemically alters the structure of sulfur-bearing heterocycles at the sulfur heteroatom(s) thereof or at sites adjacent to said heteroatoms. Thus, sulfur-bearing heterocycles are converted into molecules having structures such as the structures of compounds (b)–(h), shown in FIG. 1. Polar substituents can be biocatalytically added to the sulfur heteroatom as shown for compounds (d) and (e), disrupting the planar structure of the molecule and thereby preventing the formation of stable, highly organized intermolecular interactions. Alternatively, heterocyclic rings can be broken open as shown for compounds (b), (c), (f), (g) and (h), producing sites of free rotation that similarly prevent the formation of stable intermolecular interactions. Certain biocatalysts convert sulfur-bearing heterocycles into molecules having both polar substituents and sites of free rotation, as shown for compounds (f), (g) and (h). The hydrocarbon framework of the sulfur-bearing heterocycle is not substantially altered as a result of biocatalytic action. Therefore, the fuel value of the treated, low viscosity petroleum liquid produced according to the present invention is not significantly degraded.

Biocatalytic conversion of sulfur-bearing heterocycles into molecules that do not produce viscosity can proceed via a reductive (anaerobic) pathway, such that molecules similar to compounds (b) or (c) of FIG. 1, or a mixture thereof, are produced. Thus, preparations of the microorganism disclosed by Kim et al. (1990), Degradation of organic sulfur compounds and the reduction of dibenzothiophene to biphenyl and hydrogen sulfide by *Desulfovibrio desulfuricans* M6, 12 BIOTECH. LETT. (No. 10) 761–764, can be used as a reductive viscosity reducing biocatalyst in the present invention.

Alternatively, an oxidative (aerobic) pathway can be followed, such that molecules similar to compounds (d), (e), (f), (g) or (h) of FIG. 1, or a mixture thereof, are produced. Examples of microorganisms that act by this oxidative pathway, preparations of which are suitable for use as the biocatalyst in the present invention include the microbial consortium (a mixture of several microorganisms) disclosed in Kilbane (1990), 3 RESOUR. CONSERV. RECYCL.

69–79, the microorganisms disclosed by Kilbane in U.S. Pat. No. 5,002,888 (issued Mar. 26, 1991), U.S. Pat. No. 5,104,801 (issued Apr. 14, 1992) [also described in Kilbane (1990), Biodesulfurization: future prospects in coal cleaning, in PROC, 7TH ANN. INT'L. PITTSBURGH COAL CONF. 373–382], and U.S. Pat. NO. 5,198,341 (issued Mar. 30, 1993); and by Omori et al. (1992), Desulfurization of dibenzothiophene by *Corynebacterium* sp. strain SY1, 58 APPL. ENV. MICROBIOL. (NO. 3) 911–915.

Each of the foregoing microorganisms can function as a biocatalyst in the present invention because each produces one or more enzymes (protein catalysts) that carry out the specific chemical reactions by which sulfur-bearing heterocycles are converted into molecules that lack the physicochemical properties condusive to viscosity. Lehninger, PRINCIPLES OF BIOCHEMISTRY (Worth Publishers, Inc., 1982), p. 8–9; cf. C. E. Zobell at column 1 (line 54) to column 2 (line 4) and at column 11 (lines 25–28) of U.S. Pat. No. 2,641,564 (issued Jun. 9, 1953) and E. E. Kern et al. at column 3 (lines 4–12) of U.S. Pat. No. 5,094,668 (issued Mar. 10, 1992). Mutational or genetically engineered derivatives of any of the foregoing microorganisms can also be used as the biocatalyst herein, provided that appropriate biocatalytic function is retained.

As explained previously, enzymes are protein catalysts made by living cells. Enzymes promote, direct or facilitate the occurrence of a specific chemical reaction or series of reactions (referred to as a pathway) without themselves becoming consumed or altered as a result thereof. Enzymes can include one or more unmodified or post-translationally or synthetically modified polypeptide chains or fragments or portions thereof, coenzymes, cofactors, or coreactants which collectively carry out the desired reaction or series of reactions. The reaction or series of reactions relevant to the present invention converts sulfur-bearing heterocycles into molecules lacking the physicochemical properties condusive to viscosity. Biocatalytic enzyme preparations that are useful in the present invention include microbial lysates, extracts, fractions, subfractions, or purified products obtained from suitable microorganisms by conventional means and capable of carrying out the desired biocatalytic function. Generally, such enzyme preparations are substantially free of intact microbial cells. In U.S. Pat. No. 5,132,219 (issued Jul. 21, 1992 to Kilbane), and in pending U.S. patent application Ser. No. 07/897,314 (filed Jun. 11, 1992 by Kilbane and Monticello) and U.S. patent application Ser. No. 07/911,845 (filed Jul. 10, 1992 by Rambosek et al.) both now abandoned disclose suitable enzyme preparations.

It is preferable to prepare a BDS-active suspension of lysed microorganisms, substantially free of intact cells. Any lysis process, whether conventional or adapted from conventional techniques, can be used, provided that the enzyme responsible for BDS reactivity remains functional. For example, the ATCC No. 53968 bacteria can be subjected to one or more freeze-thaw cycles, treated with a suitable detergent and/or chaotropic agent, processed using a French press, or, more preferably, can be sonicated by conventional means comprising the use of a bath or immersion probe sonicator and incubation on melting ice.

It is particularly preferred to prepare a substantially cell-free aqueous extract of the microbial source of BDS reactivity, wherein the extract contains a substantial proportion of the total BDS activity functionally expressed by the microorganism. In certain suitable microorganisms, the BDS reactive enzyme may be functionally expressed as a cell envelope-associated enzyme. In the case of the ATCC No. 53968 microorganism and its functional derivatives, it was previously disclosed in U.S. application Ser. No. 07/586,597, now abandoned, that BDS activity appears to arise from an enzyme associated with the exterior cell membrane and/or cell wall of the intact bacterium.

A cell free extract suitable for use as biocatalyst in the present BDS method can be prepared according to standard techniques, such as centrifugal fractionation, ammonium sulfate fractionation, filtration, bioaffinity or immunoaffinity precipitation, gel permeation chromatography, liquid chromatography, high pressure liquid chromatography, reverse-phase liquid chromatography, preparative electrophoresis, isoelectric focussing, and the like. For example, a centrifugal fractionation procedure, wherein it is shown that a substantial proportion of ATCC No. 53968 expressed BDS reactivity is associated with the "cell debris" fraction of sonicated, lysed bacterial cells. This fraction, which comprises fragments of cell walls and/or outer cell membranes, was obtained as a pellet following centrifugation of lysed ATCC No. 53968 cells for 5 minutes at 6,000× g.

In another embodiment, recombinant enzymes can be employed. These enzymes can be prepared by methods known in the art, such as by complementation, as exemplified below.

Mutant strains of a *R. rhodochrous*, which are incapable of cleaving carbon-sulfur bonds, are produced by exposing a strain of *R. rhodochrous* to a mutagen to produce *R. rhodochrous* mutants. Suitable strains of *R. rhodochrous* include any strain of *R. rhodochrous* containing DNA which encodes a biocatalyst capable of selective cleavage of carbon-sulfur bonds, such as ATCC No. 53968 as reported in U.S. Pat. No. 5,104,801, the teachings of which are incorporated herein by reference. In one embodiment, the IGTS8 strain of *R. rhodochrous*, from Institute of Gas Technology (Chicago, Ill.) is used.

Suitable mutagens include radiation, such as ultraviolet radiation or chemical mutagens, such as N-methyl-N'-nitrosoguanidine (NTG), hydroxylamine, ethylmethane-sulphonate (EMS) and nitrous acid.

*R. rhodochrous* mutants are allowed to grow in an appropriate medium and screened for carbon-sulfur bond cleavage activity. Mutants without carbon-sulfur bond cleavage activity are labelled $CS^-$. Any method of screening which allows for an accurate detection of carbon-sulfur bond cleavage activity is suitable in the method of the present invention. Suitable methods of screening for this activity include exposing the different mutants to carbon-sulfur bond containing molecules and measure carbon-sulfur bond cleavage. In a preferred embodiment, the mutants are exposed to DBT, whose breakdown product, 2-hydroxybiphenyl (2-HBP), fluoresces under short wave ultraviolet light. Other methods include gas and liquid chromatography, infrared and nuclear magnetic resonance spectra. See Kodama, et al., Applied and Environmental Microbiology, pages 911–915 (1992) and Kilbane and Bielaga, Final Report D.O.E. Contract No. DE-AC22-88PC8891 (1991). Once $CS^-$ mutants are identified and isolated, clones are propagated for further analysis.

Concurrent with the mutagenesis of one culture of *R. rhodochrous*, a second culture is maintained, *R. rhodochrous*, that expresses a substance with carbon-sulfur bond cleavage activity ($CS^+$). DNA is extracted from this organism. Various methods of DNA extraction are suitable for isolating the DNA of this organism. Suitable methods include phenol and chloroform extraction. See Maniatis et al., *Molecular Cloning, A Laboratory Manual*, 2d, Cold Spring Harbor Laboratory Press, page 16.54 (1989), herein referred to as Maniatis et al.

Once the DNA is extracted from *R. rhodochrous*, the DNA is cut into fragments of various kilobase lengths, collection of which makes up the DNA library. Various methods of fragmenting the DNA of *R. rhodochrous* to free the DNA of the present invention, may be used including enzymatic and mechanical methods. Any four-base recognition restriction endonuclease such as TaqI or Sau 3A is suitable for fragmenting the DNA. Suitable methods of fragmenting DNA can be found in Maniatis et al.

The various DNA fragments are inserted into several mutant clones of *R. rhodochrous*, with the purpose of isolating the fragment of DNA, which encodes a biocatalyst. The transformation of a previously CS$^-$ mutant cell to a CS$^+$ transformed cell is evidence that the inserted DNA fragment encodes a biocatalyst. Any method of inserting DNA into *R. rhodochrous* which allows for the uptake and expression of said fragment is suitable. In a preferred embodiment, electroporation is used to introduce the DNA fragment into *R. rhodochrous*. See Maniatis et al.

Once transformed mutant *R. rhodochrous* has been produced and identified, DNA fragment encoding the CS$^+$ biocatalyst can be identified and isolated. The encoded biocatalyst can then be produced using the isolated DNA in various methods well-known and readily available to those skilled in the art. In addition the isolated DNA can be sequenced and replicated by methods known by those skilled in the art (See Maniatis et al.).

DNA isolated by the above described method can be isolated from any organism which expresses a biocatalyst capable of selectively cleaving carbon-sulfur bonds in a sulfur-bearing hydrocarbon. They include *Bacillus sphaericus* ATCC No. 53969 as reported in U.S. Pat. No. 5,002,888, the teachings of which are incorporated herein by reference.

Other methods of isolating the DNA of the present invention, include variations on the rational used above. For example, it would be possible to randomly insert a CS$^-$ DNA plasmid into clones of a CS$^+$ strain of *R. rhodochrous*. DNA encoding a CS$^+$ biocatalyst could then be identified by screening for clones that have been transformed from CS$^+$ to CS$^-$.

The recombinant DNA molecule of the present invention is intended to encompass any DNA resulting from the insertion into its chain, by chemical or biological means, a gene encoding a biocatalyst capable of selectively cleaving carbon-sulfur bonds, said gene not originally present in that chain. Recombinant DNA includes any DNA created by procedures using restriction nucleases, nucleic acid hybridization, DNA cloning, DNA sequencing or any combination of the preceding. Methods of construction can be found in Maniatis et al., and in other methods known by those skilled in the art. The term "recombinant DNA", as used herein, is intended to encompass any DNA resulting from the insertion into the chain, by chemical or biological means, of a DNA not originally present in that chain.

Procedures for the construction of DNA plasmid vectors of the present invention include those described in Maniatis et al. and other methods known by those skilled in the art. Suitable plasmid vectors include pRF-29 and pRR-6. The term "DNA plasmid vector" is intended any replication competent vector which has the capability of having DNA inserted into it and, subsequently, the expression of that DNA insert by an appropriate host cell. In addition, the plasmid vector must be receptive to the insertion of a DNA plasmid containing the genes of the present invention where the gene encodes a biocatalyst which has the capability to selective cleave carbon-sulfur bonds. Procedures for the construction of DNA plasmid vectors include those described in Maniatis et al. and others known by those skilled in the art.

The plasmids of the present invention include any DNA fragment containing the genes of a DNA which encode a biocatalyst which has the capability to selective cleave carbon-sulfur bonds. The term "plasmid" is intended to encompass any DNA fragment. The DNA fragment should be transmittable to a host microorganism by transformation or conjugation. Procedures for the construction or extraction of DNA plasmids include those described in Maniatis et al. and others known by those skilled in the art.

The transformed microorganisms of the present invention can be created by various methods by those skilled in the art. For example, transfection electroporation as explained by Maniatis et al. can be used. By the term "microorganisms" or "organism" is intended any organism capable of the uptake and expression of foreign DNA, i.e., DNA not originally a part of the organism nuclear material. Suitable organisms may include Corynebacterium or Escherichia.

In certain microorganisms that are suitable for use as the viscosity reducing biocatalyst herein, the enzyme responsible for biocatalytic cleavage of carbon-sulfur bonds is present on the exterior surface (e.g., the cell envelope) of the intact microorganism. Thus, non-viable (e.g., heat-killed) preparations of such microorganisms can be used as a carrier for an enzyme biocatalyst. Non-viable preparations of *Rhodococcus rhodochrous* ATCC No. 53968 can be used in this manner. Enzyme preparations suitable for use herein can be immobilized on or affixed to other types carrier, such as membranes, filters, polymeric resins, glass particles or beads, or ceramic particles or beads. The use of immobilized enzyme biocatalyst preparations facilitates the separation of the biocatalyst from the treated, low viscosity petroleum liquid manufactured according to the present invention.

Several investigators have disclosed methods for producing microorganisms that are suitable for use as the biocatalyst of the present invention. These methods involve culturing preparations of microorganisms obtained from natural sources such as sewage sludge, petroleum refinery wastewater, garden soil, or coal tar-contaminated soil under selective culture conditions in which the microorganisms are grown in the presence of sulfur-bearing heterocycles as the sole sulfur source; exposing the microbial preparation to chemical or physical mutagens; or a combination of these methods. Such techniques are recounted by Isbister and Doyle in U.S. Pat. No. 4,562,156 (issued Dec. 31, 1985); by Kilbane in 3 RESOUR. CONSERV. RECYCL. 69–79 (1990), U.S. Pat. Nos. 5,002,888, 5,104,801 and 5,198,341; and by Omori and coworkers in 58 APPL. ENV. MICROBIOL. (No. 3) 911–915 (1992).

In certain preferred embodiments, viscous petroleum liquids are subjected to biocatalytic treatment according to the present invention, using biocatalyst preparations of the *Rhodococcus rhodochrous* microorganism disclosed by Kilbane in U.S. Pat. No. 5,104,801. This microorganism has been deposited at the American Type Culture Collection (ATCC), 12301 Park Lawn Drive, Rockville, Md., U.S.A. 20852 on Nov. 28, 1989 under the terms 0f the Budapest Treaty, and has been designated as ATCC Deposit No. 53968. One suitable ATCC No. 53968 biocatalyst preparation is a culture of the living microorganisms, prepared generally as described in U.S. Pat. No. 5,104,801 and in prior U.S. patent application Ser. No. 07/631,642 now abandoned. Intact heat-killed ATCC No. 53968 microorganisms can also be used, as can cell-free enzyme preparations obtained from ATCC No. 53968 generally as described in U.S. Pat. No. 5,132,219 and in pending U.S. patent application Ser. No. 07/897,314 now abandoned.

In the biocatalytic viscosity reducing method described herein, the viscous petroleum liquid in need of treatment is combined with the biocatalyst preparation. The relative amounts of biocatalyst preparation and petroleum liquid can be adjusted to suit particular conditions, or to produce a particular level of residual viscosity in the treated petroleum liquid. The amount of biocatalyst preparation to be combined with a given quantity of viscous petroleum liquid will reflect the nature, concentration and specific activity of the particular biocatalyst used, as well as the type of viscous petroleum liquid being treated, the degree of viscosity thereof and the degree of viscosity reduction sought or considered acceptable.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms (e.g., ATCC No. 53968) is used as the biocatalyst preparation, a suitable culture medium lacking a sulfur source other than sulfur-bearing heterocycles can be inoculated with suitable microorganisms and fermented until a desired culture density is reached. The resulting culture can be diluted with additional medium or another suitable buffer, or microbial cells present in the culture can be retrieved e.g., by centrifugation, and resuspended at a greater concentration than that of the orginal culture. The concentrations of non-viable microorganism and of enzyme biocatalyst preparations can be adjusted similarly. In this manner, appropriate volumes of biocatalyst preparations having predetermined specific activities and/or concentrations can be obtained.

The volume and relative concentration of a given biocatalyst preparation needed for treatment is also related to the nature and identity of the viscous petroleum liquid. Petroleum liquids that are very high in sulfur-bearing heterocycles, or liquids for which a large reduction in viscosity is sought will require treatment by biocatalysts of high specific activity and/or high concentration. It is preferable to minimize the degree to which the viscous petroleum liquid must be diluted with the biocatalyst; thus, smaller volumes of higher concentration and/or specific activity biocatalyst preparations are preferred. As a general rule., it is preferable that the biocatalyst preparation not exceed one-tenth of the volume of the combined biocatalyst and viscous petroleum liquid during treatment. In some embodiments, the biocatalyst is added in substantially nonaqueous or solid form. For example, nonaqueous formulations of enzyme biocatalysts, or immobilized enzyme biocatalysts, can be used.

Other conditions that affect the rate and extent of viscosity reduction according to the present invention include the physical conditions to which the viscous petroleum liquid/biocatalyst preparation mixture is exposed. The mixture can be incubated at any temperature between the pour point of the petroleum liquid and the temperature at which the biocatalytic agent is inactivated. Preferably, biocatalytic viscosity reduction is carried out at a temperature between about 10° C. and about 60° C. Ambient temperature is preferred when using biocatalyst preparations of or derived from ATCC No. 53968 microorganisms. If desired, the mixture can be subjected to mechanical agitation to accelerate the rate of viscosity reduction by ensuring thorough and even distribution of the biocatalyst preparation in the viscous petroleum liquid. Suitable means for introducing mechanical agitation include, for example, incubation in a stirred-tank reactor. Alternatively, the viscous petroleum liquid can be caused to flow through or over a filter, membrane or other solid support to which an immobilized biocatalyst preparation is affixed.

The mixture of biocatalyst and petroleum liquid can be incubated for a predetermined period of time, a sufficient period of time for the desired level of residual viscosity to be attained, or for an indefinite period of time. In many embodiments, there is no need to remove the biocatalyst preparation before embarking on various refining procedures, in view of the fact that the biocatalyst does not significantly degrade the fuel value of the petroleum liquid. Thus, removal of the biocatalyst is incidental to other refining procedures such as desalting, dewatering, centrifugation or distillation. Biocatalyst recovery may advantageously be achieved by using immobilized biocatalyst preparations, which can readily be separated from the treated petroleum liquid. Thus, enzymes immobilized on a resin or on beads can be recovered by centrifugation, and enzymes affixed to membranes or filters can be recovered, e.g., by filtering the treated petroleum therethrough. Incubation with the biocatalyst need not be an isolated step, but may be conducted during the recovery, transit or storage of the substrate petroleum liquids.

If an oxidative or aerobic biocatalyst is used (e.g., ATCC No. 53968 microorganisms and enzymes obtained therefrom), and it is desired to increase the level of oxygen present in the biocatalyst/petroleum liquid mixture, oxygen can be supplied to the viscous petroleum liquid prior to treatment or during biocatalysis, using conventional techniques such as sparging or bubbling an oxygen source therethrough, or agitating the mixture during biocatalysis under an aerobic atmosphere. Air, compressed air, oxygen enriched air or purified oxygen can be used. It is preferable to add the oxygen source directly to the viscous petroleum liquid, due to the greater solubility of oxygen in petroleum, relative to its solubility in aqueous systems.

As noted above, non-viable microorganism or enzyme biocatalysts can be used under conditions other than the conditions needed to maintain the viability of a culture of biocatalytic microorganisms. Nonaqueous media such as perfluorochemicals (PFCs), which are known to have a high capacity to dissolve oxygen, may be used to reconstitute or suspend such a biocatalyst preparation. Oxygen-rich non-aqueous media may accelerate the rate of biocatalysis by an oxidative biocatalyst.

The progress of biocatalytic viscosity reduction can be monitored by several known techniques that are readily available. Suitable techniques include, but are not limited to, the collection of baseline and timecourse samples of the liquid being treated for direct analysis of viscosity in instruments such as a properly calibrated Saybolt viscometer. Alternatively, the disappearance of sulfur-bearing heterocycles and/or the appearance of non-viscosity producing molecules formed therefrom by biocatalytic action can be monitored using a gas chromatograph coupled with mass spectrophotometric detection (GC/MS), or with atomic emission spectral detection (flame spectrometry, GC/AES). In this manner, either the physical or chemical effects of biocatalytic viscosity reduction can be monitored, once suitable calibration curves have been established.

EQUIVALENTS

Those skilled in the art will recognize, or be able to ascertain using no more than routine experimentation, many equivalents to the specific embodiments of the invention described herein. These and all other such equivalents are intended to be encompassed by the following claims.

We claim:

1. A method for reducing the viscosity of a viscous petroleum liquid which contains sulfur-bearing heterocycles, the physicochemical properties of said heterocycles contributing significantly to the viscosity of said petroleum liquid, the method comprising combining said petroleum liquid with an aqueous phase containing a bacterial biocatalyst that converts sulfur-bearing heterocycles into molecules having physicochemical properties that result in reduction of viscosity of the treated petroleum liquid.

2. The method of claim 1 wherein the biocatalyst converts sulfur-bearing heterocycles into said molecules by selectively cleaving at least one carbon-sulfur bond in said heterocycles, thereby breaking open heterocyclic rings and producing sites of free rotation in said molecules.

3. The method of claim 1 wherein the biocatalyst selectively oxidizes the sulfur-bearing heterocycles at the sulfur heteroatoms thereof.

4. The method of claim 3 wherein the biocatalyst oxidatively cleaves carbon-sulfur bonds in said heterocycles at sites adjacent to the sulfur heteroatoms thereof.

5. The method of claim 1 wherein the viscous petroleum liquid is heavy crude oil or bitumen.

6. The method of claim 1 wherein the biocatalyst is selected from the group consisting of:

a preparation of one or more bacterial that selectively cleave at least one carbon-sulfur bond in said heterocycles, thereby breaking open heterocyclic rings and producing sites of free rotation in said molecules;

b) a preparation of bacterial extract, lysate, fraction or subfraction obtained from said bacterial; and c) a preparation that is a mixture of said microbial organisms and said bacterial extract, lysate, fraction or subfraction.

7. The method of claim 6 wherein the biocatalyst oxidatively cleaves at least one carbon-sulfur bond in said heterocycle.

8. The method of claim 7 wherein the biocatalyst is a preparation of *Rhodococcus rhodochrous* bacteria, ATCC No. 53968 or a extract, lysate, fraction or subfraction obtained therefrom.

9. The method of claim 8 wherein the biocatalyst is a culture of *Rhodococcus rhodochrous* bacteria, ATCC No. 53968.

10. A method for reducing the viscosity of viscous petroleum, wherein said petroleum contains sulfur-bearing heterocycles, the physicochemical properties of said heterocycles contributing significantly to the viscosity of said petroleum liquid, the method comprising combining said petroleum liquid with a preparation of an aqueous phase containing one or more bacterial that convert sulfur-bearing heterocycles into molecules having physicochemical properties that result in reduction of viscosity of the treated petroleum liquid.

11. The method of claim 10 wherein the bacterial selectively oxidize the sulfur-bearing heterocycles at the sulfur heteroatoms thereof.

12. The method of claim 10 wherein the bacterial oxidatively cleave carbon-sulfur bonds in said heterocycles at sites adjacent to the sulfur heteroatoms thereof.

13. The method of claim 10 wherein the viscous petroleum is heavy crude oil or bitumen.

14. A method for reducing the viscosity of viscous petroleum, wherein said petroleum contains sulfur-bearing heterocycles, the physicochemical properties of said heterocycles contributing significantly to the viscosity of said petroleum liquid, the method comprising combining said petroleum liquid with a preparation of a bacterial extract, lysate, fraction or subfraction that converts sulfur-bearing heterocycles into molecules having physicochemical properties that result in reduction of viscosity of the treated petroleum liquid, said bacterial extract, lysate, fraction or subfraction being obtained from one or more bacterial.

15. The method of claim 14 wherein the preparation selectively oxidizes the sulfur-bearing heterocycles at the sulfur heteroatoms thereof.

16. The method of claim 14 wherein the preparation cleaves carbon-sulfur bonds in said heterocycles at sites adjacent to the sulfur heteroatoms thereof.

17. The method of claim 14 wherein the preparation is obtained from *Rhodococcus rhodochrous* bacteria, ATCC No. 53968.

* * * * *

UNITED STATES PATENT AND TRADEMARK OFFICE
CERTIFICATE OF CORRECTION

Page 1 of 2

PATENT NO.   :   5,529,930
DATED        :   June 25, 1996
INVENTOR(S)  :   Daniel J. Monticello and William M. Haney, III It is certified that error appears in the above-indentified patent and that said Letters Patent is hereby corrected as shown below:

Column 13, line 29: After the word "more", delete "bacterial" and insert therefor --bacteria--;

Column 13, line 33: After the word "of", insert the word --a--;

Column 13, line 34: After the word "said", delete the word "bacterial" and insert therefor --bacteria--;

Column 13, lines 35-36: After the word "said", delete the words "microbial organisms" and insert therefor --bacteria--;

Column 14, line 15: After the word "the", delete the word "bacterial" and insert therefor --bacteria--;

Column 14, line 18: After the word "the", delete the word "bacterial" and insert therefor --bacteria--;

UNITED STATES PATENT AND TRADEMARK OFFICE
CERTIFICATE OF CORRECTION

PATENT NO. : 5,529,930

DATED : June 25, 1996

INVENTOR(S) : Daniel J. Monticello, et al.

It is certified that error appears in the above-indentified patent and that said Letters Patent is hereby corrected as shown below:

Column 14, line 34: After the word "more", delete the word "bacterial" and insert therefor --bacteria--.

Signed and Sealed this

Tenth Day of September, 1996

Attest:

BRUCE LEHMAN

*Attesting Officer*   *Commissioner of Patents and Trademarks*